(12) United States Patent
Amalric et al.

(10) Patent No.: US 7,652,130 B2
(45) Date of Patent: *Jan. 26, 2010

(54) USE OF ALKYLPOLYXYLOSIDES IN COSMETICS

(75) Inventors: Chantal Amalric, Blan (FR); Alicia Roso, Saix (FR); Nelly Michel, Maisons-Alfort (FR); Guy Tabacchi, Paris (FR); Alain Milius, Nice (FR); Jean-Pierre Boiteux, Chemin du Fargaolou (FR); Hervé Rolland, Castres (FR)

(73) Assignee: Societe d'Exploitation de Produits pour les Industries Chimiques SEPPIC, Paris (FR)

( * ) Notice: Subject to any disclaimer, the term of this patent is extended or adjusted under 35 U.S.C. 154(b) by 446 days.

This patent is subject to a terminal disclaimer.

(21) Appl. No.: 10/491,756

(22) PCT Filed: Sep. 30, 2002

(86) PCT No.: PCT/FR02/03328

§ 371 (c)(1),
(2), (4) Date: Aug. 9, 2004

(87) PCT Pub. No.: WO03/030861

PCT Pub. Date: Apr. 17, 2003

(65) Prior Publication Data

US 2004/0265259 A1     Dec. 30, 2004

(30) Foreign Application Priority Data

Oct. 5, 2001   (FR) .................................. 01 12821

(51) Int. Cl.
*A61K 31/7028* (2006.01)
*C07G 3/00* (2006.01)
*C07H 15/04* (2006.01)

(52) U.S. Cl. ............................ 536/4.1; 514/25; 514/53; 514/54; 514/61

(58) Field of Classification Search ............. 514/772.4, 514/398; 536/123.1
See application file for complete search history.

(56) References Cited

U.S. PATENT DOCUMENTS

| | | | | |
|---|---|---|---|---|
| 5,605,651 | A | * | 2/1997 | Balzer ........................ 424/401 |
| 5,681,949 | A | * | 10/1997 | Johansson et al. ......... 536/123.1 |
| 5,952,395 | A | * | 9/1999 | Lorant ...................... 514/772.4 |
| 6,667,396 | B2 | | 12/2003 | Milius et al. |
| 6,670,306 | B2 | * | 12/2003 | Milius et al. ................ 504/206 |
| 7,229,632 | B2 | * | 6/2007 | Amalric et al. ............. 424/401 |

FOREIGN PATENT DOCUMENTS

EP        0649867     *    4/1995
FR      2 807 435          10/2001

* cited by examiner

*Primary Examiner*—Shaojia Anna Jiang
*Assistant Examiner*—Eric S Olson
(74) *Attorney, Agent, or Firm*—Young & Thompson

(57) ABSTRACT

A composition, method of preparation, and use to enhance the cosmetic feel of oil-in-water emulsions based upon the addition to the oil in water emulsion of one or more alkylpolyxylosides represented by formula:

$R-O-(X)_p,$ wherein p is a decimal number between 1 and 5,
wherein X is a xylose residue, and
wherein R is a branched alkyl radical represented by the formula:

$CH(C_nH_{2n+1})(C_mH_{2m+1})-CH_2-$ wherein m is an integer between 6 and 12, n is an integer between 8 and 16, and the sum of m+n is in the range of from about 14 to 26.

21 Claims, No Drawings

USE OF ALKYLPOLYXYLOSIDES IN COSMETICS

BACKGROUND OF THE INVENTION

1. Field of the Invention

The subject of the present invention is the use of particular alkylpolyxylosides as agents enhancing the cosmetic feel of oil-in-water emulsions containing a polymer, and the oil-in-water emulsions containing such alkylpolyxylosides.

2. Related Art

Cosmetic emulsions with an aqueous continuous phase (that is to say of the oil-in-water or O/W type) increasingly frequently contain polymers which are used as thickeners, emulsifiers or stabilizers. The use of these polymers make it possible to reduce or eliminate the quantity of traditional emulsifiers. However, the feel of the cosmetic compositions thus obtained loses in richness and becomes aqueous.

Patent application FR 00 04414, filed on 6 Apr. 2000, describes compounds of formula:

$$R\text{—}O\text{—}(X)_p$$

in which:
p represents a decimal number between 1 and 5,
X represents a xylose residue, and
R represents a branched alkyl radical of formula:

$$CH(C_nH_{2n+1})(C_mH_{2m+1})\text{—}CH_2\text{—}$$

in which m is an integer between 6 and 18, n is an integer between 4 and 18 and the sum n+m is greater than or equal to 10.

These compounds are recommended as surfactants.

It has now been discovered that alkylpolyxylosides obtained from a Guerbet alcohol having from 16 to 28 carbon atoms make it possible to enhance the feel of oil-in-water emulsions containing a polymer.

SUMMARY OF THE INVENTION

The invention provides a composition, as well as a method of preparation, comprising at least one alkylpolyxyloside represented by formula (I);

$$R\text{—}O\text{—}(X)_p \quad (I),$$

wherein p is a decimal number between 1 and 5,
wherein X is a xylose residue, and
wherein R is a branched alkyl radical represented by the formula:

$$CH(C_nH_{2n+1})(C_mH_{2m+1})\text{—}CH_2\text{—}$$

wherein m is an integer between 6 and 12, n is an integer between 8 and 16, and the sum of m+n is in the range of from 14 to 26. The addition of this composition to an oil-in-water emulsion enhances the cosmetic feel of the emulsion.

DETAIL OF THE DESCRIPTION OF EMBODIMENTS

Thus, according to a first aspect, the subject of the invention is the use of an alkylpolyxyloside of formula:

$$R\text{—}O\text{—}(X)_p \quad (I)$$

in which:
p represents a decimal number between 1 and 5,
X represents a xylose residue, and
R represents a branched alkyl radical of formula:

$$CH(C_nH_{2n+1})(C_mH_{2m+1})\text{—}CH_2\text{—}$$

in which m is an integer between 6 and 12, n is an integer between 8 and 16 and the sum n+m is in the range from 14 to 26;

or alternatively of a composition consisting of a mixture of at least two alkylpolyxylosides as defined above;

as agent enhancing the cosmetic feel of water-in-oil emulsions containing one or more polymers.

Preferably, the sum n+m is equal to 14, 16, 18, 22 or 26 and R represents more particularly a 2-hexyldecyl (m=6, n=8), 2-octyldecyl (m=8, n=8), 2-hexyldodecyl (m=6, n=10), 2-octyldodecyl (m=8, n=10), 2-decyltetradecyl (m=10, n=12) or 2-dodecylhexadecyl (m=12, n=14) radical. In a particularly preferred manner, the sum m+n is greater than 16, and is advantageously equal to 18, 22 or 26, more preferably still equal to 22 or 26.

In formula $R\text{—}O\text{—}(X)_p$, the group $R\text{—}O\text{—}$ is linked to X by the anomeric carbon of the xylose residue, so as to form an acetal functional group.

p, which represents the average degree of polymerization of the xylose, is more particularly between 1 and 2.5, and most particularly between 1 and 2.0.

The compound of formula $R\text{—}O\text{—}(X)_p$ may be prepared by reacting xylose with an excess of a fatty alcohol of formula ROH, and then removing the unreacted fatty alcohol.

In the process as defined above, the reaction is carried out in the presence of strong acid catalysts.

According to one variant of the process as defined above, the xylose is reacted with an alcohol of formula $R_1\text{—}OH$, in which $R_1$ contains from 1 to 4 carbon atoms and more particularly with butanol, to give the acetal of formula $R_1O\text{—}(X)_p$, which then undergoes transacetalization with an excess of alcohol of formula ROH with distillation of the alcohol of formula $R_1OH$ formed and then removal of the unreacted alcohol of formula ROH.

In this process and its variant, as described above, the removal of the unreacted alcohol of formula ROH is carried out according to methods known to persons skilled in the art such as for example distillation, thin-film distillation, molecular distillation or solvent extraction.

According to a second aspect, the subject of the present invention is an oil-in-water emulsion comprising:
  from 0.1 to 15% by weight of one or more alkylpolyxylosides as defined above;
  from 0.05 to 10% by weight of one or more polymers;
  more than 5% by weight, preferably more than 7% by weight, and more preferably still more than 10% by weight, and up to 50% by weight of a fatty phase consisting of one or more oils and/or one or more waxes.

According to an advantageous embodiment, the alkylpolyxyloside of formula (I) is in the form of a mixture with its corresponding Guerbet alcohol (of formula ROH where R has the meaning given above), in an alkylpolyxyloside/alcohol weight ratio in the range from 1/99 to 99/1.

Among the polymers used in the oil-in-water emulsion according to the present invention, there may be mentioned in particular homopolymers or copolymers of acrylic acid, acrylic acid derivatives, acrylamide and its derivatives, acrylamidomethylpropanesulfonic acid, vinyl monomer, trimethylaminoethylacrylate chloride such as for example the products marketed under the name CARBOPOL® Ultrez 10, PEMULEN® TR1 and TR2, SIMULGEL®A, SIMULGEL®NS, SIMULGEL®EPG, SIMULGEL®EG, LUVIGEL®EM, SALCARE®SC91, SALCARE®SC92, SALCARE®SC95, SALCARE®SC96, FLOCARE®ET100, HISPAGEL®, SEPIGEL®305, SEPI- GEL®501, SEPIGEL®502, FLOCARE®ET58, STABILEZE®06; hydrocolloids of plant or biosynthetic origin such as for example xanthan gum, karaya gum, carrageenans, alginates; silicates, cellulose and its derivatives; starch and its hydrophilic derivatives; polyurethanes.

Among the oils which can be used in the context of the present invention, there may be mentioned in particular:

- oils of plant origin, such as sweet almond oil, copra oil, castor oil, jojoba oil, olive oil, rapeseed oil, peanut oil, sunflower oil, wheatgerm oil, corn germ oil, soybean oil, cottonseed oil, alfalfa oil, poppy seed oil, pumpkinseed oil, evening primrose oil, millet oil, barley oil, rye oil, safflower oil, candlenut oil, passion flower oil, hazelnut oil, palm oil, shea butter, apricot kernel oil, calophyllum oil, sisymbrium oil, avocado oil, calendula oil;
- vegetable oils and their ethoxylated methyl esters;
- oils of animal origin, such as squalene, squalane;
- mineral oils such as paraffin oil, liquid paraffin and isoparaffins;
- synthetic oils, in particular fatty acid esters such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lanolate, isocetyl lanolate, monoglycerides, diglycerides and triglycerides of fatty acids, such as glyceryl triheptanoate, alkyl benzoates, poly-alpha-olefins, polyolefins such as polyisobutene, synthetic isoalkanes such as isohexadecane, isododecane, perfluorinated oils and silicone oils.

Among the waxes which can be used in the context of the present invention, there may be mentioned for example beeswax; carnauba wax; candelilla wax; ouricoury wax; Japan wax; cork fiber or sugarcane wax; paraffin waxes; lignite waxes; microcrystalline waxes; lanolin wax; ozokerite; polyethylene wax; hydrogenated oils; silicone waxes; vegetable waxes; fatty alcohols and fatty acids which are solid at room temperature; glycerides which are solid at room temperature.

The water-in-oil emulsion in accordance with the present invention may also optionally contain up to 15% by weight of an emulsifier.

Among the emulsifiers which can be used in the context of the present invention, there may be mentioned for example fatty acids; ethoxylated fatty acids; fatty acid esters of sorbitol; ethoxylated fatty acid esters; polysorbates; polyglycerol esters; ethoxylated fatty alcohols; sucrose esters; alkylpolyglycosides; sulfated and phosphated fatty alcohols.

In a manner known per se, these emulsions may additionally comprise one or more compounds chosen from humectants, such as for example glycerin, preservatives, colorants, perfumes, cosmetic active agents, inorganic or organic sunscreens, inorganic fillers such as iron oxides, titanium oxides and talc, synthetic fillers such as nylons and polymethyl methacrylates which are crosslinked or not, silicone elastomers, sericites and plant extracts.

The oil-in-water emulsions in accordance with the invention may be prepared in the following manner.

The aqueous phase is heated to a temperature of 70 to 85° C. In parallel, the fatty phase containing the emusifying system of the invention and the oils (optionally additivated with waxes, coemulsifiers and lipophilic active agents) is heated to an identical temperature of 70 to 85° C. The two phases are then mixed and emulsified with the aid of a rotor-stator type emulsifier (for example a SILVERSON laboratory mixer). After a few minutes of emulsification, the emulsion is cooled with gentle stirring. The polymer(s) are introduced into the oily phase, into the aqueous phase or directly into the emulsion according to the recommendations of the suppliers.

If all the components of the emulsion are liquid, the manufacture may be carried out without heating.

EXAMPLES

The invention will be illustrated with the following examples.

Example 1

Preparation of a 2-decyltetradecylxyloside 61.8 kg of 2-decyltetradecanol, marketed by the company SASOL under the name Isofol®24, are introduced into a reactor. 8.7 kg of xylose are gradually dispersed in the stirred medium and 65 g of sulfuric acid are then added. The mixture is kept at 115° C. for 6 hours, under a partial vacuum, and then neutralized with caustic soda. After filtration, the clear liquid obtained has a hydroxyl value of 183 and contains 15% by weight of 2-decyltetradecylxyloside and 85% by weight of 2-decyltetradecanol.

Example 2

Demonstration of the Feel Enhancement Obtained when the Compound According to Example 1 is Added to Cosmetic Preparations Containing No Emulsifier Two series of emulsions having the following compositions are prepared:

| 1st series | |
|---|---|
| Cetearyl octanoate | 10% |
| Water | qsp 100% |
| Polymer | qs |
| Preservatives | qs |
| 2nd series | |
| Compound according to example 1 | 3% |
| Cetearyl octanoate | 10% |
| Water | qsp 100% |
| Polymer | qs |
| Preservatives | qs |

Mode of preparation: the polymer is dispersed in water and neutralized if necessary, and then cetearyl octanoate is introduced into the gel formed. Homogenization of the emulsion is carried out without heating, by stirring with traditional items of equipment. The compound according to example 1 is added with cetearyl octanoate.

The preparations obtained are O/W emulsions.

A sensory evaluation is carried out on a panel of 20 trained volunteers. The results are presented in table 1. Each criterion is scored from 0 to 5.

TABLE 1

| Polymer | Polyacrylamide and C11-13 isoparaffin and laureth-7: 3% | Carbomer 0.4% and acrylates/ steareth-20 methacrylate copolymer 0.2% | Acryloyl dimethyl taurate copolymer 1% |
|---|---|---|---|
| Evaluation of the emulsions without the compound according to example 1 | | | |
| Richness | 2 | 0 | 0 |
| Residual film | 2 | 1 | 1 |
| Evaluation of the emulsions containing 3% of the compound according to example 1 | | | |
| Richness | 3 | 2 | 3 |
| Residual film | 4 | 3 | 3 |

The addition of 3% of the compound according to example 1 to the polymer-based emulsions significantly enhances the richness and increases the sensation of emollience, leaving a residual film significantly perceived by the volunteers.

Example 3

Demonstration of the Feel Enhancement Obtained when the Compound According to Example 1 is Added to Cosmetic Preparations Containing an Emulsifier Two emulsions having the following composition are prepared:

| Emulsifier | 3% | 3% |
|---|---|---|
| Compound according to example 1 | | 3% |
| Cetearyl octanoate | 10% | 10% |
| Water | qs 100% | qs 100% |
| Polyacrylamide and C11-13 isoparaffin and laureth-7 | 1.5% | 1.5% |
| Preservatives | qs | qs |

The preparation of these emulsions is carried out according to a conventional process by emulsification in the hot state of 2 aqueous and oily phases.

The preparations obtained are O/W emulsions.

A sensory evaluation is carried out on a panel of 20 trained volunteers. The results are presented in table 2. Each criterion is scored from 0 to 5.

TABLE 2

| Emulsifier | Arachidyl alcohol and behenyl alcohol and arachidyl glucoside | PEG 100 stearate and glyceryl stearate | Ceteth 2 + ceteth 21 |
|---|---|---|---|
| Evaluation of the trials without the compound according to example 1 | | | |
| Richness | 1 | 1 | 0 |
| Residual film | 1 | 1 | 1 |
| Evaluation of the trials containing 3% of the compound according to example 1 | | | |
| Richness | 3 | 2 | 2 |
| Residual film | 3 | 3 | 3 |

The addition of 3% of the compound according to example 1 makes it possible to significantly enhance the sensory profile of the emulsions tested by simultaneously increasing the richness and the residual film.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

The invention claimed is:

1. A composition to enhance the cosmetic feel of oil-in-water emulsions comprising:
   a fatty phase; and
   at least one alkylpolyxyloside, wherein,
   said composition is free of an aqueous phase, and
   said alkylpolyxyloside is represented by formula (I):

$$R\text{—}O\text{—}(X)_p \quad (I),$$

wherein said p is the average degree of polymerization, and is a decimal number between 1 and 5,
   wherein said X is a xylose residue, and
   wherein said R is a branched alkyl radical represented by the formula:

$$CH(C_nH_{2n+1})(C_mH_{2m+1})CH_2\text{—};$$

wherein said m is an integer in the range of from 6 to 12,
   wherein said n is an integer in the range of from 8 to 16, and
   wherein the sum m+n is in the range of from 14 to 26.

2. The composition according to claim 1, wherein said p is between 1 and 2.5.

3. The composition according to claim 2, wherein p is between 1 and 2.0.

4. The composition according to claim 1, wherein the sum m+n is equal to at least one integer selected from the group consisting of:
   a) 14,
   b) 16,
   c) 18,
   d) 22, and
   e) 26.

5. The composition according to claim 4, wherein said sum is greater than 16.

6. The composition according to claim 4, wherein said sum is equal to 18.

7. The composition according to claim 4, wherein said sum is equal to 22.

8. The composition according to claim 4, wherein said sum is equal to 26.

9. The composition according to claim 1, wherein said R is at least one component selected from the group consisting of:
   a) 2-hexyldecyl,
   b) 2-octyldecyl,
   c) 2-hexyldodecyl,
   d) 2-octyldodecyl,
   e) 2-decyltetradecyl, and
   f) 2-dodecylhexadecyl radical.

10. An oil-in-water emulsion composition comprising:
    an aqueous phase;
    more than 5% by weight of a fatty phase; and
    from 0.1 to 15% by weight of at least one alkylpolyxyloside represented by formula (I)

$$R\text{—}O\text{—}(X)_p \, (I),$$

wherein said p is a decimal number between 1 and 5, wherein said X is a xylose residue, and
wherein said R is a branched alkyl radical represented by formula (II):

wherein said m is an integer in the range of from 6 to 12,
wherein said n is an integer in the range of from 8 to 16, and
wherein the sum of n+m is in the range of from 14 to 26.

11. The composition according to claim 10, wherein said fatty phase is up to 50% by weight of said composition.

12. The composition according to claim 11, wherein said fatty phase comprises at least one component selected from the group consisting of:
a) oils; and
b) waxes.

13. The composition according to claim 12, wherein said oil is selected from the group consisting of:

| | |
|---|---|
| a) | oils of plant origin, |
| b) | sweet almond oil, |
| c) | copra oil, |
| d) | castor oil, |
| e) | jojoba oil, |
| f) | olive oil, |
| g) | rapeseed oil, |
| h) | peanut oil, |
| i) | sunflower oil, |
| j) | wheatgerm oil, |
| k) | corn germ oil, |
| l) | soybean oil, |
| m) | cottonseed oil, |
| n) | alfalfa oil, |
| o) | poppy seed oil, |
| p) | pumpkinseed oil, |
| q) | evening primrose oil, |
| r) | millet oil, |
| s) | barley oil, |
| t) | rye oil, |
| u) | safflower oil, |
| v) | candlenut oil, |
| w) | passion flower oil, |
| x) | hazelnut oil, |
| y) | palm oil, |
| z) | shea butter, |
| aa) | apricot kernel oil, |
| bb) | calophyllum oil, |
| cc) | sisymbrium oil, |
| dd) | avocado oil, |
| ee) | calendula oil; |
| ff) | vegetable oils and their ethoxylated methyl esters, |
| gg) | oils of animal origin, such as squalene, |
| hh) | mineral oils, |
| ii) | paraffin oil, |
| jj) | liquid paraffin, |
| kk) | isoparaffins; |
| ll) | synthetic oils, |
| mm) | fatty acid esters, |
| nn) | butyl myristate, |
| oo) | propyl myristate, |
| pp) | cetyl myristate, |
| qq) | isopropyl palmitate, |
| rr) | butyl stearate, |
| ss) | hexadecyl stearate, |
| tt) | isopropyl stearate, |
| uu) | octyl stearate, |
| vv) | isocetyl stearate, |
| ww) | dodecyl oleate, |
| xx) | hexyl laurate, |
| yy) | propylene glycol dicaprylate, |
| zz) | esters derived from lanolic acid, |
| aaa) | isopropyl lanolate, |
| bbb) | isocetyl lanolate, |
| ccc) | monoglycerides, |
| ddd) | diglycerides, |
| eee) | triglycerides of fatty acids, |
| fff) | glyceryl triheptanoate, |
| ggg) | alkyl benzoates, |
| hhh) | poly-alpha-olefins, |
| iii) | polyolefins, |
| jjj) | polyisobutene, |
| kkk) | synthetic isoalkanes, |
| lll) | isohexadecane, |
| mmm) | isododecane, |
| nnn) | perfluorinated oils, and |
| ooo) | silicone oils. |

14. The composition according to claim 12, wherein said wax comprises at least one component selected from the group consisting of:

| | |
|---|---|
| a) | beeswax, |
| b) | carnauba wax, |
| c) | candelilla wax, |
| d) | ouricoury wax, |
| e) | Japan wax, |
| f) | cork fiber, |
| g) | sugarcane wax, |
| h) | paraffin waxes, |
| i) | lignite waxes, |
| m) | microcrystalline waxes, |
| n) | lanolin wax, |
| o) | ozokerite, |
| p) | polyethylene wax, |
| q) | hydrogenated oils, |
| r) | silicone waxes, |
| s) | vegetable waxes, |
| t) | fatty alcohols, |
| u) | fatty acids, and |
| v) | glycerides. |

15. The composition according to claim 10, wherein said alkylpolyxyloside is in the form of a mixture with its corresponding alcohol of formula ROH.

16. The composition according to claim 15, wherein the weight ratio of alkylpolyxyloside/alcohol is in the range of from 1/99 to 99/1.

17. The composition according to claim 10, wherein the sum of m+n is equal at least one integer selected from the group consisting of:
a) 14,
b) 16,
c) 18,
d) 22, and
e) 26.

18. The composition according to claim 17, wherein said integer is greater than 16.

19. The composition according to claim 17, wherein said integer is greater than or equal to 22.

20. The composition according to claim 17, wherein said integer is greater than or equal to 26.

21. The composition according to claim 10, wherein said R is at least one component selected from the group consisting of:
a) 2-hexyldecyl,
b) 2-octyldecyl,
c) 2-hexyldodecyl,
d) 2-octyldodecyl,
e) 2-decyltetradecyl, and
f) 2-dodecylhexadecyl.

* * * * *